United States Patent [19]

Karrer et al.

[11] 4,017,536
[45] Apr. 12, 1977

[54] ETHER AND THIOETHER CONTAINING THIOLESTERS

[75] Inventors: Friedrich Karrer, Basel; Saleem Farooq, Aesch, both of Switzerland

[73] Assignee: Ciba-Geigy Corporation, Ardsley, N.Y.

[22] Filed: May 27, 1975

[21] Appl. No.: 581,070

Related U.S. Application Data

[62] Division of Ser. No. 521,314, Nov. 6, 1974, Pat. No. 3,900,507.

[30] Foreign Application Priority Data

Nov. 9, 1973 Switzerland .................. 15812/73
Nov. 9, 1973 Switzerland .................. 15813/73
Oct. 9, 1974 Switzerland .................. 13565/74

[52] U.S. Cl. .............................................. 260/470
[51] Int. Cl.² ........................................ C07C 149/40
[58] Field of Search ................................ 260/470

[56] References Cited

UNITED STATES PATENTS 3,829,489  8/1974  Edamura et al. ............... 260/455 R Primary Examiner—Howard T. Mars
Attorney, Agent, or Firm—Frederick H. Rabin

[57] ABSTRACT

New compounds of the formula

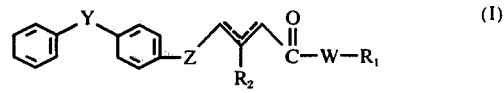

wherein $R_1$ represents $C_1$–$C_4$-alkyl, $R_2$ represents methyl or ethyl, Y represents O, —$CH_2$, C=O or S, and one of the radicals Z or W stands for oxygen, while the other represents sulphur, are disclosed, a process for their preparation and a method for combating pests by applying the compounds to the said pests.

3 Claims, No Drawings

ETHER AND THIOETHER CONTAINING THIOLESTERS

This is a division of application Ser. NO. 521,314 filed on Nov. 6, 1974 now U.S. Pat. No. 3,900,507.

The present invention relates to compounds of the formula

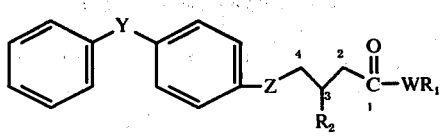
(I)

wherein
$R_1$ represents $C_1-C_4$-alkyl,
$R_2$ represents methyl or ethyl,
Y represents O, $-CH_2-$, $>C=O$ or S, and one of the radicals Z or W stands for oxygen, while the other represents sulphur.

Compounds of formula I preferred by virtue of their action are those wherein
$R_1$ represents methyl, ethyl or isopropyl,
$R_2$ represents methyl,
Y represents O, $-CH_2-$, $>C=O$ or S, and one of the radicals Z or W stands for oxygen, while the other represents sulphur.

Compounds of formula I are produced in a manner known per se by, for example, the following reactions:

for alkyl, M for a metal, preferably an alkali metal, and X for halogen, preferably for chlorine or bromine.

The processes A to D are performed at normal pressure. For the obtainment in process D of a higher rate of reaction, it is also possible to use increased pressure and elevated temperature.

The reaction temperatures, which are not very critical, are in most cases between $-10°$ and $140°$ C; the reaction is often performed at the boiling point of the applied solvent, preferably at $0°$ to $70°$ C.

Suitable solvents for the aforementioned processes are as follows:

Process A: inert solvents, for example: ketones such as acetone, methyl ethyl ketone, cyclohexanone, also dimethylsulphoxide, dimethylformamide and dimethoxyethane.

Process B: for example, ethers such as tetrahydrofuran, dimethoxyethane, dioxane, also hexamethylphosphonic acid triamide or dimethylformamide, optionally in admixture with the above-mentioned ethers.

Process C: inert solvents, particularly hydrocarbons such as benzene, toluene, xylene and hexane.

Process D: for example: hexamethylphosphoric acid triamide, dimethylformamide, and others; it is however also possible to operate without solvents or diluents.

Suitable bases for Process A are, e.g. anhydrous alkali carbonates, alkali alkoxides or alkali hydrides. Bases suitable in the case of Process B are, for example, alkali metal hydrides, alkaline-earth metal hydrides, alkali metal hydroxides and alkali metal alkoxides. And

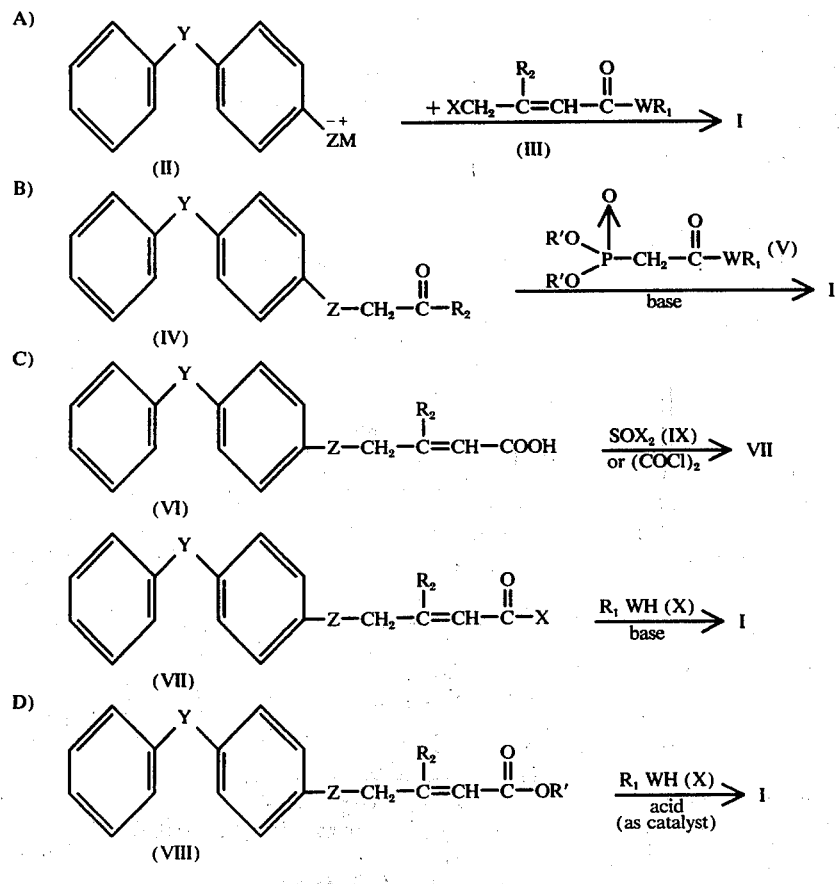

In formulae II to X, the symbols $R_1$, $R_2$, Y, Z and W have the meanings given for formula I, and R' stands preferred bases for Process C are organic bases, such as trialkylamines or pyridine.

Starting materials of formulae II, III, IV, V, VI and VII are known; thus, for example, the compounds of formula III can be prepared by the process described in J. Org. Chem. 24, 434 (1959).

In the preparation of compounds of formula I by the aforementioned processes, the two possible geometric isomers can be formed in reciprocal proportions. The described compounds constitute in some cases mixtures of the cis- and trans-isomers.

Pure isomers can be obtained, e.g. by application of starting products of uniform configuration in the synthesis of the active substances of formula I, or by fractional distillation, or gas- or adsorption-chromatographical separation processes from the mixture of cis- and trans-isomers.

In the preparation of compounds of formula I, there can be formed in the above-mentioned Process B), in which in the final stage of synthesis (WITTIG-HORNER reaction) a double bond is formed in the $\Delta^{2,3}$-position of the side chain, the two geometrical isomers (cis/trans-isomers).

In Processes (A), (C) and (D), the proportions of the geometrical isomers (double bond in the 2,3-position) are given by the applied starting and intermediate products III, VI or VIII, and do not change during synthesis.

The compounds of formula I in which finally there exists a double bond in the 3,4-position of the side chain (vinyl ether) can be prepared by transformation of the compounds having a double bond in the 2,3-position by isomerisation. By migration of the double bond from the 2,3-position to the 3,4-position, there are obtained from (primarily formed) allyl ethers of formula I vinyl ethers of formula I. The preparation of such vinyl ethers is described in Example 2 (see page 14), and is effected, for example, from an allylic ether I primarily formed by a WITTIG-HORNER reaction, under the reaction conditions given therein.

The geometrical isomers of allylic ethers of formula I having a double bond in the 2,3-position can be easily separated by chromatographical separation processes into cis- and trans-isomers, whereas this was not possible to attain in the case of the geometrical isomers of the vinylic ethers of formula I (with double bond in the 3,4-position).

The presence of an isomer mixture and its proportions of cis- and trans-isomers in vinyl ethers of formula I can however be clearly established by proton resonance spectroscopy.

The compounds of formula I can be used as cis/trans isomer mixtures or as pure isomers for the control of insects. The said compounds are suitable for the control of insects of the families: Tettigonidae, Gryllidae, Gryllotalpidae, Blattidae, Reduviidae, Phyrrhocoridae, Cimicidae, Delphacidae, Aphididae, Diaspididae, Pseudococcidae, Scarabaeidae, Dermestridae, Coccinellidae, Tenebrionidae, Chrysomelidae, Bruchidae, Tineidae, Noctuidae, Lymatriidae, Pyrallidae, Culicidae, Tipulidae, Stomoxydae, Trypetidae, Muscidae, Calliphoridae and Pulicidae.

The insecticidal action can be appreciably broadened and adapted to suit given circumstances by the addition of known insecticides and/or acaricides as well as insect bait. Suitable additives are, e.g.: organic phosphorus compounds, derivatives of nitrophenols, formamidines, ureas, carbamates and chlorinated hydrocarbons.

The compounds of formula I can be used on their own or together with suitable carriers and/or additives. Suitable carriers and additives may be solid or liquid, and they correspond to the substances common in formulation practice, such as, for example, natural or regenerated substances, solvents, dispersing agents, wetting agents, adhesives, thickeners, binders and/or fertilisers.

For application, the compounds of formula I can be processed into the form of dusts, emulsion condentrates, granulates, dispersions, sprays or solutions, the formulation of these preparations being effected in a manner commonly known in practice.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:

solid preparations:
dusts, scattering agents, granulates, coated granulates, impregnated granulates and homogeneous granulates;

liquid preparations:
a. water-dispersible active-substance concentrates: wettable powders, pastes or emulsions;
b. solutions.

The content of active substance in the above described agents is generally between 0.1 and 95%; it is mentioned in this connection that in the case of application from an aeroplane, or by means of other suitable application devices, concentrations of up to 99.5%, or even the pure substance, can be employed.

The active substances of formula I can be formulated, for example, as follows:

Dusts:
The following substances are used in the preparation of (a) a 5% dust, and (b) a 2% dust:
a. 5 parts of active substance,
95 parts of talcum;
b. 2 parts of active substance,
1 part of highly dispersed silicic acid,
97 parts of talcum.

The active substances are mixed and ground with the carriers.

Granulate:
The following substances are used to prepare a 5% granulate:
5 parts of active substance,
0.25 part of epichlorohydrin,
0.25 part of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The solution thus obtained is sprayed onto kaolin, and the acetone is subsequently evaporated off in vacuo.

Wettable powder:
The following constituents are used for the preparation of (a) a 40%, (b) and (c) a 25%, and (d) a 10% wettable powder:
a. 40 parts of active substance,
5 parts of sodium lignin sulphonate,
1 part of sodium dibutyl-naphthalene sulphonate,
54 parts of silicic acid;
b. 25 parts of active substance,
4.5 parts of calcium lignin sulphonate, 1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;
c. 25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselguhr,
46 parts of kaolin;
e. 10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, and the mixture is then ground in the appropriate mills and rollers. Wettable powders are obtained which can be diluted with water to give suspensions of any desired concentration.

Emulsifiable concentrates:
The following substances are used to prepare (a) a 10% and (b) a 25% emulsifiable concentrate:
a. 10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;
b. 25 parts of active substance,
2.5 parts of epoxidised vegetable oil,
10 parts of an alkylarylsulphonate/fatty alcohol polyglycol ether mixture,
5 parts of dimethylformamide,
57.5 parts of xylene.

From these concentrates it is possible to prepare, by dilution with water, emulsions of any desired concentration.

Spray:
The following constituents are used to prepare a 5% spray:
5 parts of active substance,
1 part of epichlorhydrin,
94 parts of ligroin (boiling limits 160° – 190° C).

EXAMPLE 1

Preparation of 4-[(4-phenoxy)-phenoxy]-3-methyl-2-cis/transbutenic acid-thioethyl ester (cis/trans mixture) and separation of the geometrical isomers (compound with double bond in 2,3-position of the side chain).

3.2 g of sodium hydride dispersion in mineral oil (about 60% NaH) is repeatedly washed with hexane and tetrahydrofuran, and then covered with 100 ml of pure tetrahydrofuran. To this suspension under an $N_2$-protective gas atmosphere there is added dropwise at 0° C within about 30 minutes, with stirring, 21.1 g of diethylphosphoneacetic acid-thioethyl ester (B.P. 115°–118° C/0.15 Torr). After a further 30 minutes' stirring at about 10° C, a dropwise addition is made to the reaction mixture, in the course of about 30 minutes, of the solution of 19.3 g of 1-(4-phenoxy)-phenoxy-2-propanone in 100 ml of tetrahydrofuran, with the temperature being held at 10° C by slight cooling. After further stirring for one hour at this temperature, the reaction mixture is poured into ice water, and repeatedly extracted with diethyl ether. The combined organic phases are repeatedly washed with saturated sodium chloride solution and dried by means of sodium sulphate, and the solvent is completely removed in vacuo. For further purification and isomer separation, the oily residue is chromatographed on silica gel (eluant: diethyl ether/hexane 1:4), whereupon pure 4-[(4-phenoxy)-phenoxy]-3-methyl-2-cis-butenic acid-thioethyl ester ($n_D^{20}$: 1.5862) and pure 4-[(4-phenoxy)-phenoxy]-3-methyl-2-trans-butenic acid-thioethyl ester ($n_D^{20}$: 1.5923) are obtained.

NMR-spectrum of the cis-compound ($CDCl_3$/100 Mc/ δ-values in ppm):
1.23 (triplet/3H), 1.96 (doublet/3H), 2.88 (quartet/2H), 5.10 (singlet, broad/2H), 6.08 (multiplet/1H), 6.78 –7.32 (multiplet/9H).

NMR-spectrum of the trans-compound ($CDSl_3$/100 Mc/ δ-values in ppm):
1.23 (triplet/3H), 2.13 (singlet/3H), 2.88 (quartet/2H), 4.40 (singlet, broad/2H), 6.3 (multiplet/1H), 6.77 –7.31 (multiplet/9H).

EXAMPLE 2

Preparation of 4-[(4-phenoxy)-phenoxy]-3-methyl-3-cis/transbutenic acid-thioethyl ester (compound with rearranged double-bond, i.e. double bond in $\Delta^{3,4}$)

3.2 g of sodium hydride dispersion in mineral oil (about 60% NaH) is repeatedly washed with hexane and tetrahydrofuran, and then covered with 50 ml of tetrahydrofuran and 35 ml of dimethylformamide. To this suspension present under an $N_2$-protective gas atmosphere there is added dropwise at about 10° C in the course of about 30 minutes, with stirring, 21.1 g of diethylphosphoneacetic acid-thioethyl ester. After a further 30 minutes' stirring at 10° C, the reaction mixture is cooled to 0° C; and the solution of 19.3 g of 1-(4-phenoxy)-phenoxy-2-propanone, dissolved in 35 ml of dimethylformamide, is then added dropwise to the reaction mixture; the whole is subsequently heated to room temperature and stirred for a further 20 hours at room temperature. For further processing, the contents of the flask are poured into ice water, and repeatedly extracted with diethyl ether. The combined organic phases are repeatedly washed with saturated sodium chloride solution and dried by means of sodium sulphate, and the solvent is removed in vacuo. For further purification, the oily residue is chromatographed through silica gel (eluant: diethyl ether/hexane 1:4), whereupon the pure isomer mixture of 4-[(4-phenoxy)-phenoxy]-3-methyl-3-cis/trans-butenic acid-thioethyl ester (isomer ratio about 4-5:5/ $n_D^{20}$: 1.5774) is obtained. The geometrical isomers cannot be separated from each other by layer- or column-chromatography.

NMR-spectrum of the chromatographically purified cis/transisomer mixture ($CDSl_3$/100 Mc/ δ-values in ppm.):
1.22 and 1.24 (each 1 triplet/ together 3H), 1.74 and 1.78 (each 1 doublet/ together 3H), 2.87 and 2.89 (each 1 quartet/together 2H), 3.18 and 3.43 (each 1 singlet/ together 2H), 6.37 (broad/ 1H), 6.90–7.36 (multiplet/ 9H).
The following compounds are obtained in an analogous manner:
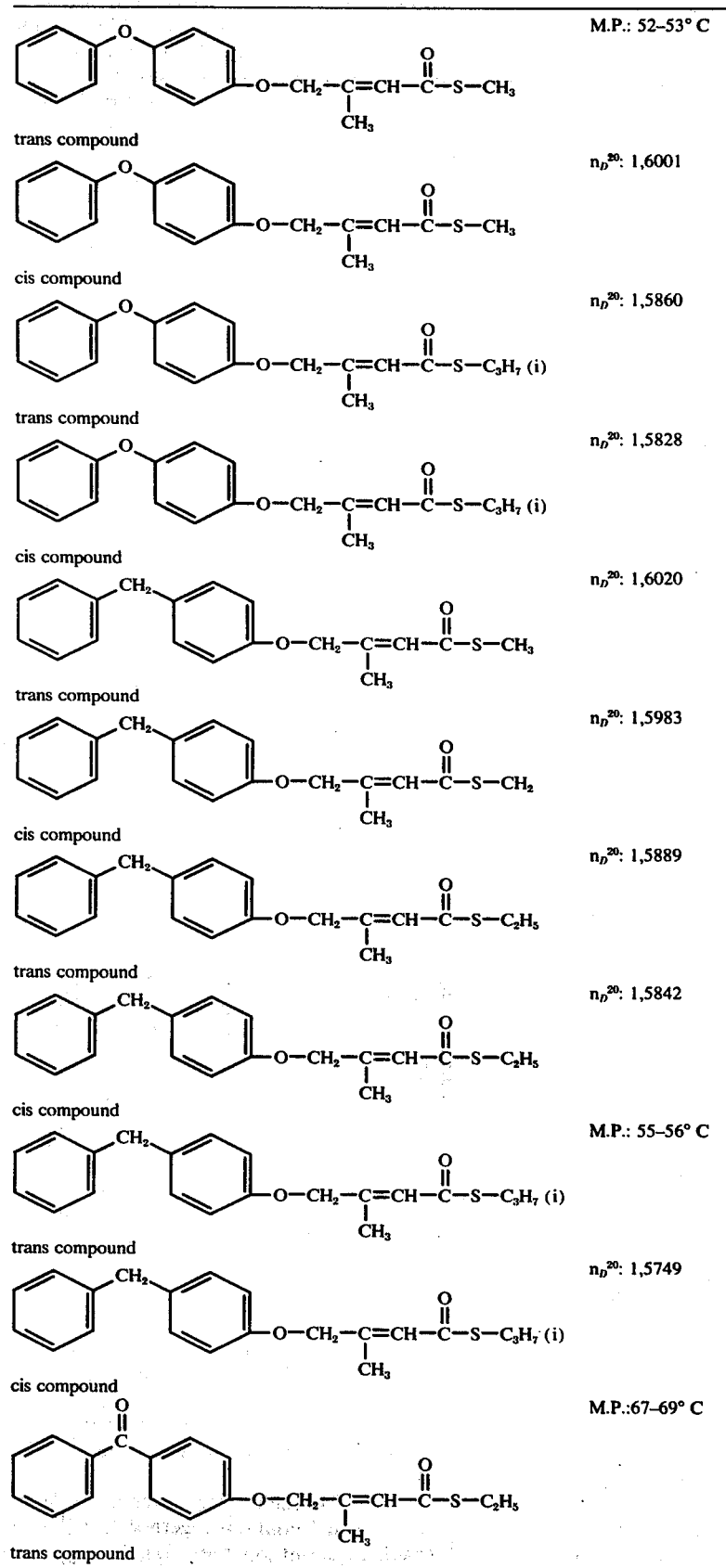
M.P.: 52–53° C
trans compound
$n_D^{20}$: 1,6001
cis compound
$n_D^{20}$: 1,5860
trans compound
$n_D^{20}$: 1,5828
cis compound
$n_D^{20}$: 1,6020
trans compound
$n_D^{20}$: 1,5983
cis compound
$n_D^{20}$: 1,5889
trans compound
$n_D^{20}$: 1,5842
cis compound
M.P.: 55–56° C
trans compound
$n_D^{20}$: 1,5749
cis compound
M.P.: 67–69° C
trans compound -continued

| Structure | |
|---|---|
| C₆H₅–S–C₆H₄–O–CH=C(CH₃)–CH₂–C(=O)–S–C₂H₅ <br> cis/trans compound | $n_D^{20}$: 1,6091 |
| C₆H₅–S–C₆H₄–O–CH₂–C(CH₃)=CH–C(=O)–S–C₃H₇ (i) <br> trans compound | $n_D^{20}$: 1,6108 |
| C₆H₅–CH₂–C₆H₄–O–CH=C(CH₃)–CH₂–C(=O)–S–C₂H₅ <br> cis/trans compound | $n_D^{20}$: 1,5751 |
| C₆H₅–O–C₆H₄–S–CH₂–C(CH₃)=CH–COOC₂H₅ <br> cis/trans compound | $n_D^{20}$: 1,5735 |
| C₆H₅–CH₂–C₆H₄–S–CH₂–C(CH₃)=CH–COOC₂H₅ <br> cis/trans compound | $n_D^{20}$: 1,5840 |
| C₆H₅–S–C₆H₄–S–CH₂–CH(CH₃)–CH₂–C(=O)–O–C₂H₅ <br> mixture of cis/trans-Δ³,⁴-compound and trans-Δ²,³-compound | $n_D^{20}$: 1,6212 |
| C₆H₅–S–C₆H₄–S–CH₂–C(CH₃)=CH–C(=O)–O–C₂H₅ <br> cis compound | $n_D^{20}$: 1,6175 |
| C₆H₅–S–C₆H₄–S–CH=C(CH₃)–CH₂–C(=O)–O–C₂H₅ <br> cis/trans compound | $n_D^{20}$: 1,6238 |

EXAMPLE 3

Contact action on Dysdercus-fasciatus larvae

A specific amount of a 0.1% acetonic active-substance solution (corresponding to 10 mg of active substance per square meter) was transferred by pipet to an aluminium dish and uniformly distributed. After evaporation of the acetone, 10 larvae in the 5th stage of Dysdercus fasciatus were placed into the treated dish containing feed and moist cotton wool. The dish was then covered with a perforated lid. After about 10 days, i.e. as soon as the control insects had moulted into adults, the test insects were examined to determine the number of normal adults.

Compounds according to Examples 1 and 2 exhibited a good action in the above test.

EXAMPLE 4

Contact action on Aedes-aegypti larvae

About 20 two-day-old larvae of the yellow-fever mosquito (Aedes aegypti) were placed in position in a beaker containing a solution of the active substance (concentration 5 ppm). The beaker was then covered with a perforated lid. After the control insects had moulted into adults, the test insects were examined and the percentage of normal adults in comparison with the control adults determined.

Compounds according to Examples 1 and 2 exhibited a good action in the above test.

EXAMPLE 5

Contact action on Tenebrio-molitor pupae

A specific amount of a 0.1% acetonic active-substance solution corresponding to 10 mg of active substance per square meter was transferred by pipet into an aluminium dish and uniformly distributed. After evaporation of the acetone, 10 freshly formed pupae were placed on the treated surface, and the dish was covered with a perforated lid. After the control insects had left the cocoon as imagines, the test insects were examined to determine the number of normal adults.

Compounds according to Examples 1 and 2 exhibited a good action in the above test.

What we claim is:

1. Compounds of the formula

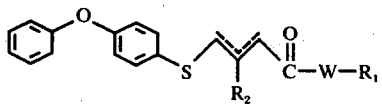

wherein
$R_1$ represents $C_1-C_4$-alkyl,
$R_2$ represents methyl or ethyl, and W represents oxygen.

2. Compounds according to claim 1, wherein
$R_1$ represents methyl, ethyl or isopropyl, and
$R_2$ represents methyl.

3. 4-[4-(Phenoxy)-phenylthio]-3-methyl-2-cis/trans-butenic acid ethyl ester according to claim 2.

* * * * *